US00PP08281P

United States Patent [19]

Zaiger et al.

[11] Patent Number: Plant 8,281

[45] Date of Patent: Jun. 29, 1993

[54] NECTARINE TREE "ROYAL GLO"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 879,854

[22] Filed: May 6, 1992

[51] Int. Cl.[5] ..... A01H 5/00

[52] U.S. Cl. ..... Plt./41.1

[58] Field of Search ..... Plt./41.1

[56] References Cited

U.S. PATENT DOCUMENTS

P.P. 7,402 12/1990 Zaiger et al. ..... Plt. 41.1

P.P. 7,891 6/1992 Zaiger et al. ..... Plt. 41.1

*Primary Examiner*—James R. Feyrer

[57] ABSTRACT

A new and distinct variety of nectarine tree which has the unique combination of outstanding features that are desirable in a new variety.

1. Heavy and regular production of a large size fruit.
2. Early maturity of the fruit.
3. Fruit having firm flesh with good handling and shipping quality.
4. Having a low winter chilling requirement of approximately 450 hours.
5. Fruit with good flavor and eating quality.
6. Relatively uniform size of fruit throughout the tree.
7. Fruit with a high degree of attractive red skin color.

1 Drawing Sheet

ORIGIN OF THE VARIETY

The present new and distinct variety of nectarine tree was originated by us in our experimental orchard located near Modesto, Calif., as a second generation cross between a selected seedling with the field identification number 12GA1100 and May Glo Nectarine (U.S. Plant Pat. No. 5,245). The selected genetic dwarf nectarine seedling "12GA1100" originated from a second generation cross between a genetic dwarf nectarine seedling of unknown parentage and Ruby Gold Nectarine (U.S. Plant Pat. No. 3,101). We grew and maintained these second generation seedlings under close observation, one such early maturing seedling, having especially desirable fruit characteristics was selected for reproduction and commercialization.

ASEXUAL REPRODUCTION OF THE VARIETY

The present new and distinct variety of nectarine tree was asexually reproduced by budding, as performed by us in our experimental orchard located near Modesto, Calif. and shows all characteristics of the tree and its fruit are established and transmitted through succeeding asexual reproductions and come to the original tree in all respects.

SUMMARY OF THE VARIETY

The new and distinct variety of nectarine tree which is of large size, vigorous, upright growth and a regular and productive bearer of large, firm, yellow flesh, clingstone fruit with good flavor and eating quality. The present variety of nectarine tree is further characterized as to its novelty by producing fruit that are relatively uniform in size throughout the tree and having a high degree of attractive red skin color. In comparison to its low chill parent May Glo Nectarine (U.S. Plant Pat. No. 5,245), the new variety requires approximately 150 hours more winter chilling, produces fruit that is larger in size and is approximately 6 days later in maturity.

PHOTOGRAPHS OF THE VARIETY

The accomanying color photographic reproductions show typical specimens of the foliage and fruit of the present new nectarine variety. The upper and lower surface of the leaves being illustrated, the exterior and a fruit divided on its suture plane to reveal flesh color, pit cavity and a stone remaining in place. The photographs were taken shortly after being picked (shipping ripe) and the colors are as nearly true as is reasonably possible in a color representation of this type.

DESCRIPTION OF THE VARIETY

The following botanical details of the present new and distinct variety of nectarine tree, its flowers, foliage and fruit are based on observation of specimens grown by us in our experimental orchard located near Modesto, Calif., with color terminology (except those in common terms) in accordance with Reinhold Color Atlas by A. Korneruf and J. H. Wanscher.

Tree:
- *Size.*—Large.
- *Vigor.*—Vigorous.
- *Growth.*—Upright.
- *Density.*—Medium dense.
- *Bearer.*—Regular.
- *Production.*—Productive.

Trunk:
- *Size.*—Medium to large.
- *Texture.*—Medium rough.
- *Color.*—Brown to grayish (5-E-3) to (5-E-4).

Branches:
- *Size.*—Medium.
- *Texture.*—Medium rough.
- *Lenticels.*—Numerous. Medium size.
- *Color.*—Light brown to brown (5-E-5) to (5-E7).

Leaves:
- *Size.*—Large.
- *Average length* — 6½".
- *Average width* — 1½".

*Texture.*—Smooth.
*Margin.*—Crenate.
*Form.*—Lanceolate.
*Thickness.*—Medium.
*Petiole.*—Medium length. Medium thickness.
*Glands.*—Reniform. Number varies from 1 to 4. Average number 3. Located on base of leaf blade and upper portion of petiole.
*Color.*—Upper surface — green to dark green (27-E-4) to (27-E-6). Lower surface — dull green to green (27-D-5) to (27-D-6).

Flower Buds:
*Size.*—Medium to large.
*Length.*—Medium.
*Form.*—Plump.

Flowers:
*Blooming period.*—Feb. 19, 1990 to Feb. 28, 1990. Varies slightly due to climatic variations.
*Size.*—Large — showy.
*Pollen.*—Present.
*Color.*—Pink.

Fruit:
*Maturity when described.*—Firm ripe.
*Date of first picking.*—May 31, 1990.
*Date of last picking.*—Jun. 6, 1990. Maturity varies slightly with climatic conditions.
*Size.*—Large. Average diameter axially — $2\frac{7}{8}''$. Average transversely in suture plane — $2\frac{5}{8}''$.
*Form.*—Nearly globose — slighty narrower at right angles to suture plane, some fruit slightly elongated.
*Suture.*—Shallow, extends from base beyond apex.
*Ventral surface.*—Slightly lipped, some fruit more on one side.
*Cavity.*—Rounded to slightly elongated in suture plane. Average depth — $\frac{3}{8}''$. Average breath — $\frac{5}{8}''$.
*Apex.*—Rounded to slight depression in suture plane.

Flesh:
*Texture.*—Firm, meaty.
*Fibers.*—Few, small, tender.
*Ripens.*—Evenly.
*Flavor.*—Mild — good balance between sugar and acid.
*Aroma.*—Slight.
*Juice.*—Moderate.
*Eating quality.*—Good.

*Color.*—Butter yellow to sunflower yellow (4-A-5) to (4-A-7).

Skin:
*Thickness.*—Medium.
*Texture.*—Medium — tenacious to the flesh.
*Tendency to crack.*—None.
*Down.*—Wanting.
*Color.*—Yellow ground color (5-A-6) to (5-A-7). Overspread with red (9-A-8) to (9-C-8).

Stone:
*Type.*—Clingstone.
*Size.*—Large. Average length — $1\frac{1}{2}''$. Average width — $1\frac{1}{8}''$. Average thickness — $\frac{3}{4}''$.
*Form.*—Ovoid.
*Base.*—Straight to slightly oblique.
*Apex.*—Cuspidate.
*Sides.*—Equal to slightly unequal.
*Surface.*—Pitted throughout, heavier toward base. Irregularly furrowed toward apex.
*Tendency to split.*—Very slight.
*Color.*—Light brown to brownish orange (6-B-6) to (6-C-6).

Use: Dessert.
*Market.*—Local and long distance.
Shipping quality: Good.
Storage Quality: Good.

The present variety of nectarine tree, its flowers, foliage and fruit herein described as grown by us in our experimental orchard under the ecological conditions prevailing near Modesto, Calif., the variety may vary in slight detail due to different climatic, soil conditions and cultural practices under which the variety may be grown.

We claim:

1. A new and distinct variety of nectarine tree, substantially as illustrated and described, characterized by its large size, vigorous, upright growth and a regular and productive bearer of large early maturing, firm, yellow flesh, clingstone fruit with good flavor and eating quality; the fruit is further characterized by having good storage and shipping quality, a high degree of attractive red skin color and in comparison to May Glo Nectarine (U.S. Plant Pat. No. 5,245) tree, the new variety has a higher winter chilling requirement of approximately 450 hours, bears fruit that is larger in size and is approximately 6 later in maturity.

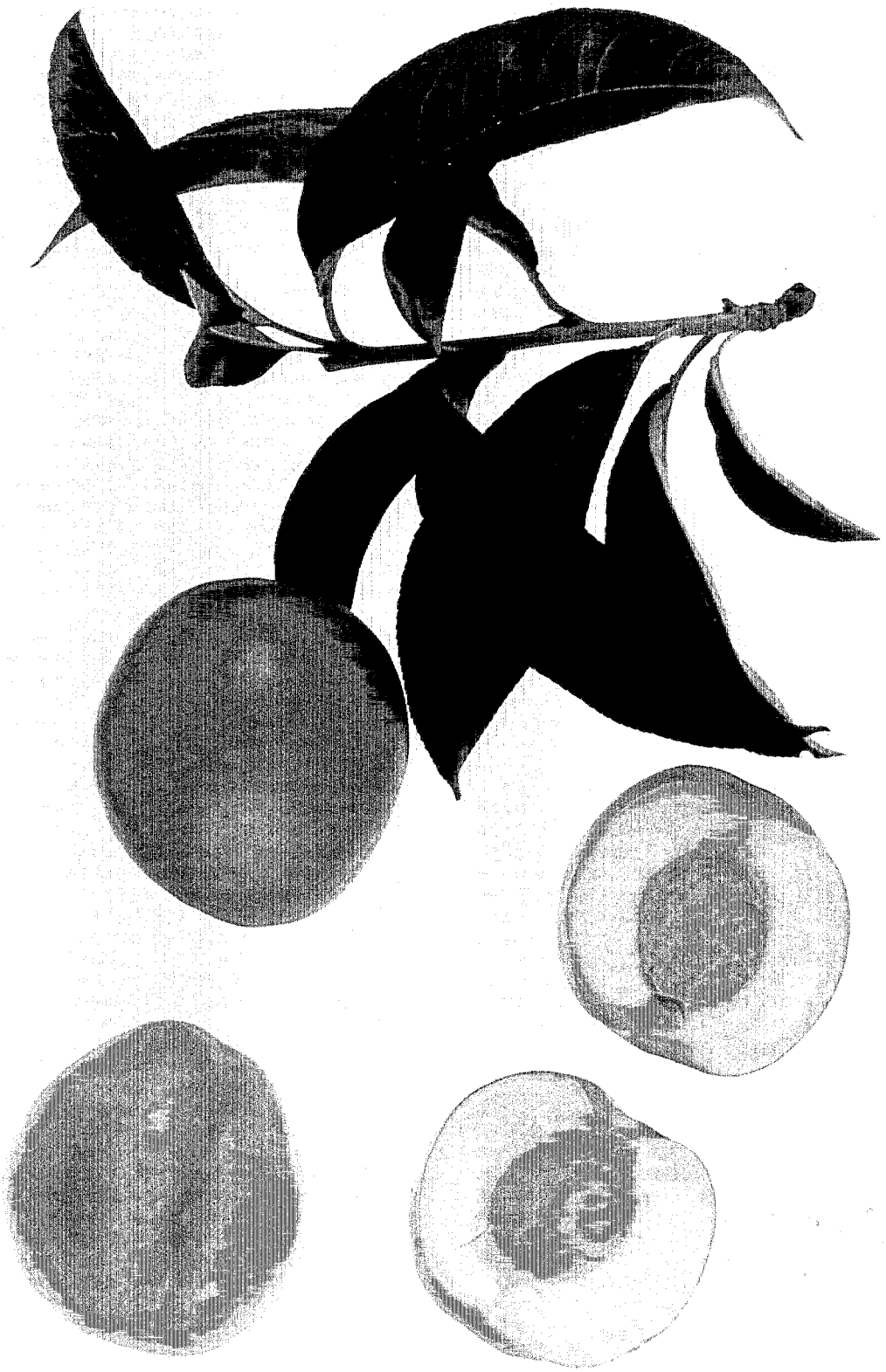

* * * * *